United States Patent
Wiederin et al.

(10) Patent No.: US 9,752,987 B1
(45) Date of Patent: Sep. 5, 2017

(54) HYDRIDE GENERATION SYSTEM

(71) Applicant: Elemental Scientific, Inc., Omaha, NE (US)

(72) Inventors: Daniel R. Wiederin, Omaha, NE (US); Austin Schultz, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 77 days.

(21) Appl. No.: 14/635,887

(22) Filed: Mar. 2, 2015

Related U.S. Application Data (60) Provisional application No. 61/946,336, filed on Feb. 28, 2014.

(51) Int. Cl.
| | |
|---|---|
| *A61L 2/00* | (2006.01) |
| *G01N 21/71* | (2006.01) |
| *B01J 4/02* | (2006.01) |
| *B01J 19/18* | (2006.01) |
| *G01N 21/73* | (2006.01) |
| *C01B 6/06* | (2006.01) |
| *C01B 6/10* | (2006.01) |

(52) U.S. Cl.
CPC ............... *G01N 21/714* (2013.01); *B01J 4/02* (2013.01); *B01J 19/18* (2013.01); *C01B 6/06* (2013.01); *C01B 6/10* (2013.01); *G01N 21/73* (2013.01); *B01J 2219/00182* (2013.01)

(58) Field of Classification Search
CPC ........... C12Q 1/68; B01L 3/0231; B01L 3/02; C12M 1/34
USPC .................... 422/300, 939; 137/885; 222/129
See application file for complete search history.

(56) References Cited

U.S. PATENT DOCUMENTS

2006/0024211 A1\* 2/2006 Giter ..................... B01L 3/0231
422/404

\* cited by examiner

*Primary Examiner* — Monzer R Chorbaji
(74) *Attorney, Agent, or Firm* — Advent, LLP (57) ABSTRACT

The present disclosure is directed to a system and a method for hydride generation. In some embodiments, the system includes an assembly for introducing hydride generation reagents into a mixing path or mixing container, where the assembly includes first chamber configured to contain a first hydride generation reagent and a second chamber configured to contain a second hydride generation reagent. A first plunger is configured to translate within the first chamber and cause a displacement of the first hydride generation reagent, and a second plunger is configured to translate within the second chamber and cause a displacement of the second hydride generation reagent. The assembly further includes base coupling the first plunger and the second plunger together.

12 Claims, 6 Drawing Sheets

HYDRIDE GENERATION SYSTEM

CROSS-REFERENCE TO RELATED APPLICATIONS

The present application claims priority under 35 U.S.C. §119(e) to U.S. Provisional Application Ser. No. 61/946,336, filed Feb. 28, 2014 and titled "HYDRIDE GENERATION SYSTEM." U.S. Provisional Application Ser. No. 61/946,336 is fully incorporated herein by reference.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. Prior or during transportation of the aliquot to the nebulizer, the sample aliquot may be mixed with hydride generation reagents and fed into a hydride gas/liquid separator that channels hydride and/or sample gas into the nebulizer. The aerosol generated by the nebulizer is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Systems and methods for hydride generation are described herein. In some embodiments, a system includes an assembly for introducing hydride generation reagents into a mixing path or mixing container, where the assembly includes first chamber configured to contain a first hydride generation reagent and a second chamber configured to contain a second hydride generation reagent. A first plunger is configured to translate within the first chamber and cause a displacement of the first hydride generation reagent, and a second plunger is configured to translate within the second chamber and cause a displacement of the second hydride generation reagent. The assembly further includes base coupling the first plunger and the second plunger together, wherein the first plunger.

A method of introducing hydride reagents into a mixing path or a mixing container can include: depositing a first hydride generation reagent in a first chamber; depositing a second hydride generation reagent in a second chamber that is rigidly connected with the first chamber; actuating the first and second chambers or a base coupled to a first plunger and a second plunger, thereby causing the first plunger to translate within the first chamber and the second plunger to translate within the second chamber to simultaneously output selected amounts of the first hydride generation reagent and the second hydride generation reagent.

A sampling system is also disclosed herein. In some embodiments, the sampling system includes a sampling assembly configured to draw a sample into a mixing path and a hydride generation assembly configured to introduce selected amounts of a first hydride generation reagent and a second hydride generation reagent into the mixing path. In some embodiments, the hydride generation assembly includes a first chamber configured to contain the first hydride generation reagent and a second chamber configured to contain the second hydride generation reagent. A first plunger is configured to translate within the first chamber and cause a displacement of the first hydride generation reagent, and a second plunger configured to translate within the second chamber and cause a displacement of the second hydride generation reagent. The first plunger and the second plunger are coupled to a common base. The sampling system may further include a nebulizer fluidically coupled with the mixing path. The nebulizer can be configured to introduce at least a portion of the sample received from the mixing path into a spray chamber. For example, the nebulizer may introduce an aerosol including at least a portion of the sample into the spray chamber. The spray chamber can then direct at least a portion of the aerosol that includes the sample (e.g., fine aerosol particles) to an analysis site (e.g., torch or plasma site) of a sample analysis instrument. For example, the spray chamber may be fluidically coupled with or form a portion of an ICP spectrometry instrument, such as an ICP-MS, ICP-AES, or the like.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. Any dimensions included in the accompanying figures are provided by way of example only and are not meant to limit the present disclosure.

FIG. 6 is a flow chart showing a method of dispensing hydride generation reagents with a hydride generation assembly, such as the hydride generation assembly illustrated in one of FIGS. 1 through 4 or the like.

DETAILED DESCRIPTION

Overview

Sample introduction systems may be employed to introduce the liquid samples into an analysis instrument, such as an ICP spectrometer (e.g., ICP-MS, ICP-OES or ICP-AES), or the like. For example, a sample introduction system may withdraw an aliquot of a liquid sample from a container and thereafter transport the aliquot to a nebulizer that converts the aliquot into a polydisperse aerosol suitable for ionization in plasma by ICP spectrometry instrumentation. Prior or during transportation of the aliquot to the nebulizer, the sample aliquot may be mixed with hydride generation reagents and fed into a hydride gas/liquid separator that channels hydride and/or sample gas into the nebulizer. This can significantly increase sensitivity to hydride-forming reagents.

In some sampling systems, hydride generation reagents (e.g., HCL and $NaBH_4$) can be withdrawn from respective containers using high-precision pumps, such as peristaltic pumps, and directed into a mixing path where they are mixed with the sample aliquot. However, peristaltic pumps must be carefully calibrated and synchronized to achieve simultaneous introduction of the hydride generation reagents in required amounts. Moreover, peristaltic pumps consume a relatively large area and/or volume, require tubing from the container to the pumps, tubing through the pumps, and tubing from the pump to the mixing path. Aside from the necessary resources and associated costs, the length of the path the reagents must travel before reaching the mixing path can increase the risk of contamination.

The present disclosure describes a hydride generation assembly that enables synchronized, simultaneous dispensing of hydride generation reagents from respective chambers by simultaneously actuating the chambers or a base coupling plungers that are configured to translate within the chambers. Accordingly, the hydride generation reagents can be fed directly from their respective holding chambers through tubes leading to the mixing path. This may greatly reduce the risk of contamination and can allow for a smaller device packaging, which may be attractive in a laboratory setting where space is limited. In some embodiments, the hydride generation assembly can include one or more additional chambers for a carrier solutions, internal standards, and any other fluids that can be simultaneously dispensed with the hydride generation reagents.

Example Implementations

FIGS. 1 through 4, illustrate a system 100 configured to generate hydrides in accordance with various embodiments of this disclosure. Those skilled in the art will appreciate that the embodiments illustrated in the drawings and/or described herein may be fully or partially combined to result in additional embodiments. Accordingly, the illustrated and described embodiments should be understood as explanatory and not as limitations of the present disclosure.

Figure 1:
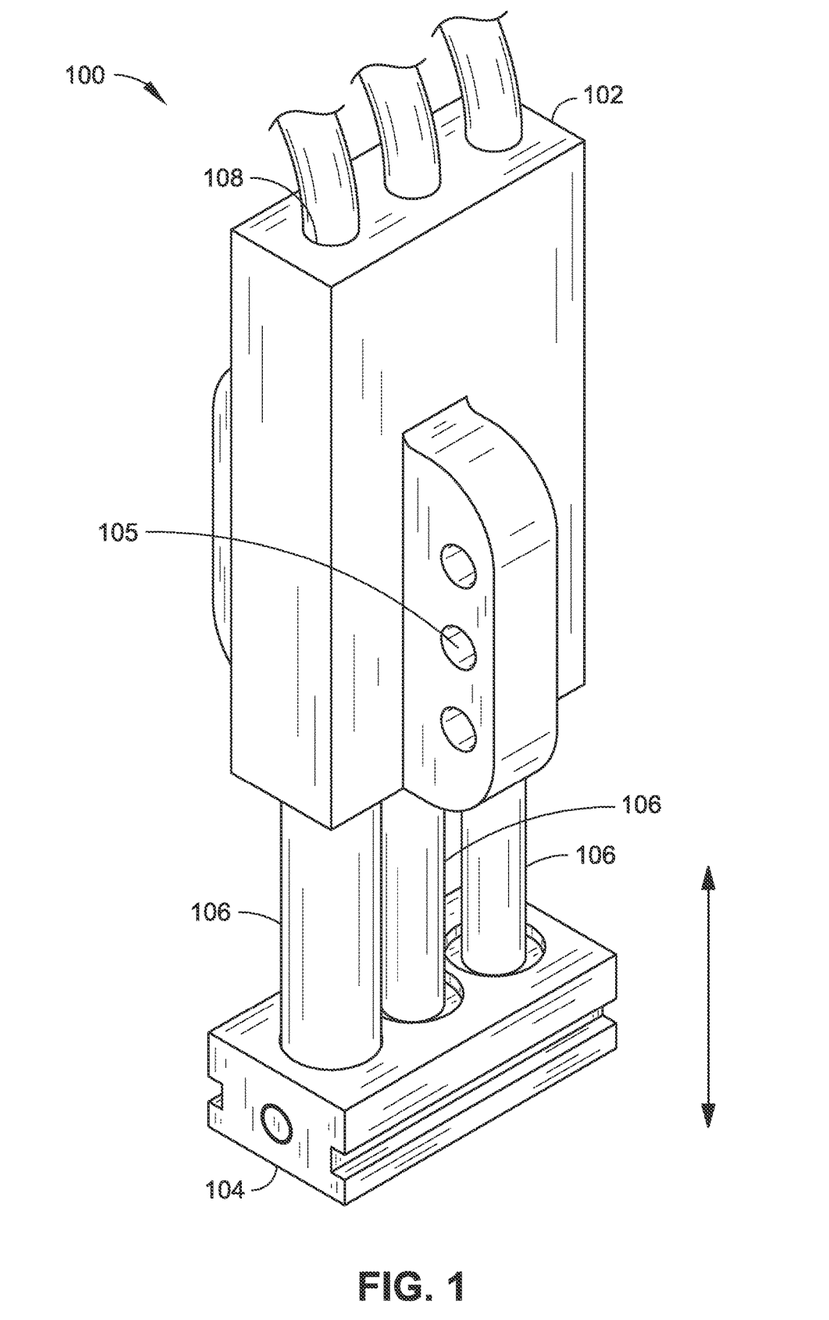
FIG. 1 is an isometric view of a hydride generation assembly, illustrated in accordance with an embodiment of this disclosure.
Figure 2:
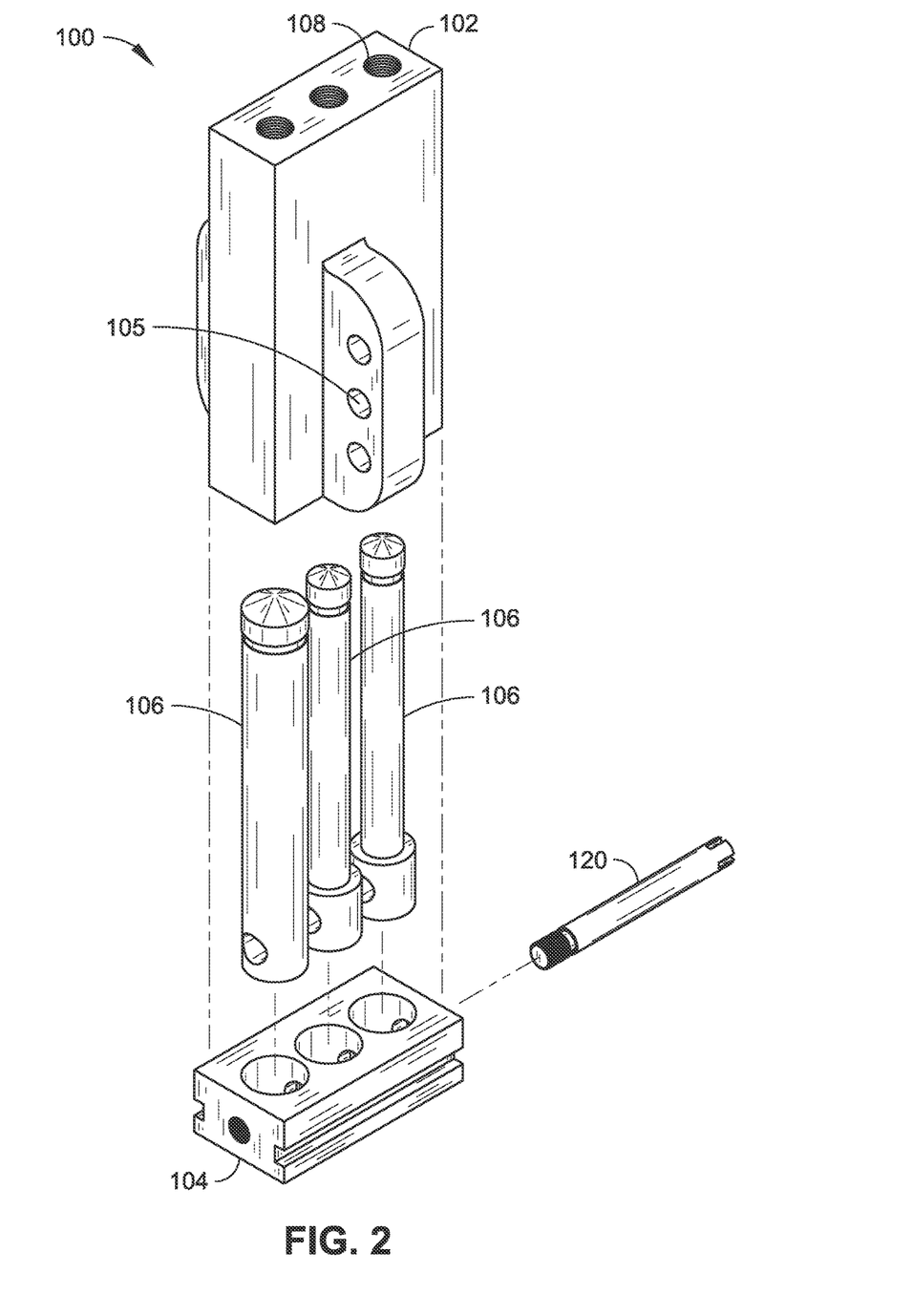
FIG. 2 is an exploded view of a hydride generation assembly, illustrated in accordance with an embodiment of this disclosure.

A hydride generation system 100 (sometimes referred to herein as a "hydride generation assembly 100") is shown in FIGS. 1 and 2. In some embodiments, two or more chambers 102 are coupled together (e.g., rigidly connected with one another) or formed in a common (e.g., monolithic) structure. For example, a first chamber and a second chamber can be formed from a single plastic mold, resulting in a common structure 102 that includes the first and second chambers, and in some embodiments, further includes one or more additional chambers. The chambers 102 may include respective outlets 108, the outlets 108 being configured for fluidically connecting the chambers 102 to a mixing path or a mixing container where the respective fluids can be simultaneously introduced. In some embodiments, the chambers 102 may include two or more mounting members 105 that enable the chambers 102 to be rigidly affixed to a rigid structure (e.g., a stationary structure or an actuatable structure). In some embodiments, the mounting members 105 may comprise holes configured to receive pins, screws, bolts, or other fasteners that hold the chambers 102 in firm contact with the rigid structure. The system 100 further includes two or more plungers 106 and a base 104 coupling the plungers 106 together. The base 104 may also include one or more mounting members that enable the base to be rigidly affixed to a rigid structure that may also be stationary or actuatable.

Figure 3:
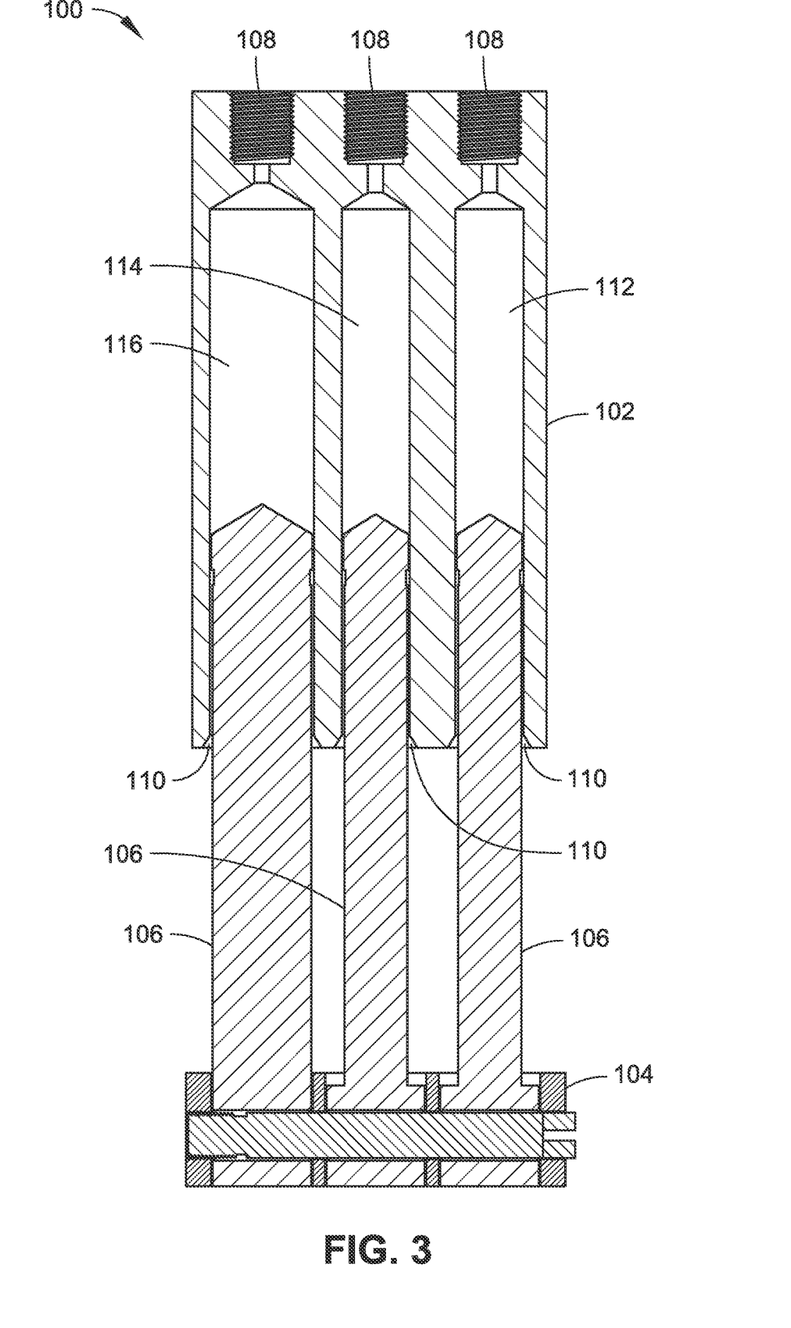
FIG. 3 is a cross-sectional view of a hydride generation assembly, illustrated in accordance with an embodiment of this disclosure.

In FIG. 3, an embodiment of the system 100 is shown to include an assembly of rigidly connected or monolithic chambers 102 including at least a first chamber 112 and a second chamber 114. The first chamber 112 and the second chamber 114 may be configured to contain hydride generation reagents. For example, the first chamber 112 may include an HCL solution, and the second chamber 114 may include a $NaBH_4$ solution, or the first and second chambers 112 and 114 may be configured to hold any other combination of hydride generation reagents (e.g., HCL and $SnCl_2$). In some embodiments, the system further includes one or more additional chambers. For example, the system 100 may include a third chamber 116 for a carrier solution, an internal standard solution, or any other fluid that can be simultaneously dispensed with the hydride generation reagents. The number of chambers and respective plungers may vary with different implementations of the system 100. For example, the system 100 may include two chambers (e.g., chamber 112 and chamber 114) and two plungers 106 coupled to the base 104, three chambers (e.g., chambers 112, 114, and 116) and three plungers 106, four chambers and four plungers, and so forth.

Each chamber (e.g., chamber 112, 114, or 116) includes at least two ports, an input 110 for receiving the respective plunger 106 and an output 108 for dispensing the fluid contained therein. In some embodiments, the output 108 is configured to connect with a tube or joint that fluidically couples the output 108 to a mixing path or a mixing container. In some embodiments, a chamber (e.g., chamber 112, 114, or 116) may be at least partially tapered and/or may include a narrow passage positioned before the output 108. The chambers and the plungers can be differently sized to facilitate different flow volumes. For example, the cross-sectional area (for a cross-section perpendicular to a direction of fluid movement) or diameter of the first chamber 112 may be different from the cross-sectional area or diameter of the second chamber 114 or the third chamber 116, and so on. By coupling the plungers 106 together with the base 104, fluid can be displaced within the chambers in a synchronized manner to generate hydrides and/or introduce selected amounts of fluids simultaneously into a common container or path. Moreover, the ratio of a first dispensed fluid (e.g., a first hydride generation reagent) to another dispensed fluid (e.g., a second hydride generation reagent) is well controlled by appropriately sizing the chambers. The synchronized motion of all the chambers 102 or all of the plungers 106 that are coupled to the base 104 causes dispensing of all associated fluids from chambers 102 in a synchronized manner with the fluid ratios held constant—of course, the concentration of each fluid can be altered to achieve specified concentration ratios. The chambers 102, however, may be sized according to default, pre-determined concentrations of the first and second hydride generation reagents. In some embodiments, the first chamber 112 and the second chamber 114 are sized appropriately to dispense the first hydride generation reagent and the second hydride generation reagent in a ratio suitable for forming a hydride when mixed with a sample. Additional chambers (e.g., the third chamber 116) can also be sized appropriately for hydride generation. For example, the first chamber 112, the second chamber 114, and the third chamber 116 may be sized appropriately to introduce the first hydride generation reagent, the second hydride generation reagent, and the carrier solution into a mixing path or mixing container in appropriate amounts relative to one another to enable a sample within the mixing path or mixing container to interact with the hydride generation reagents.

Figure 4:
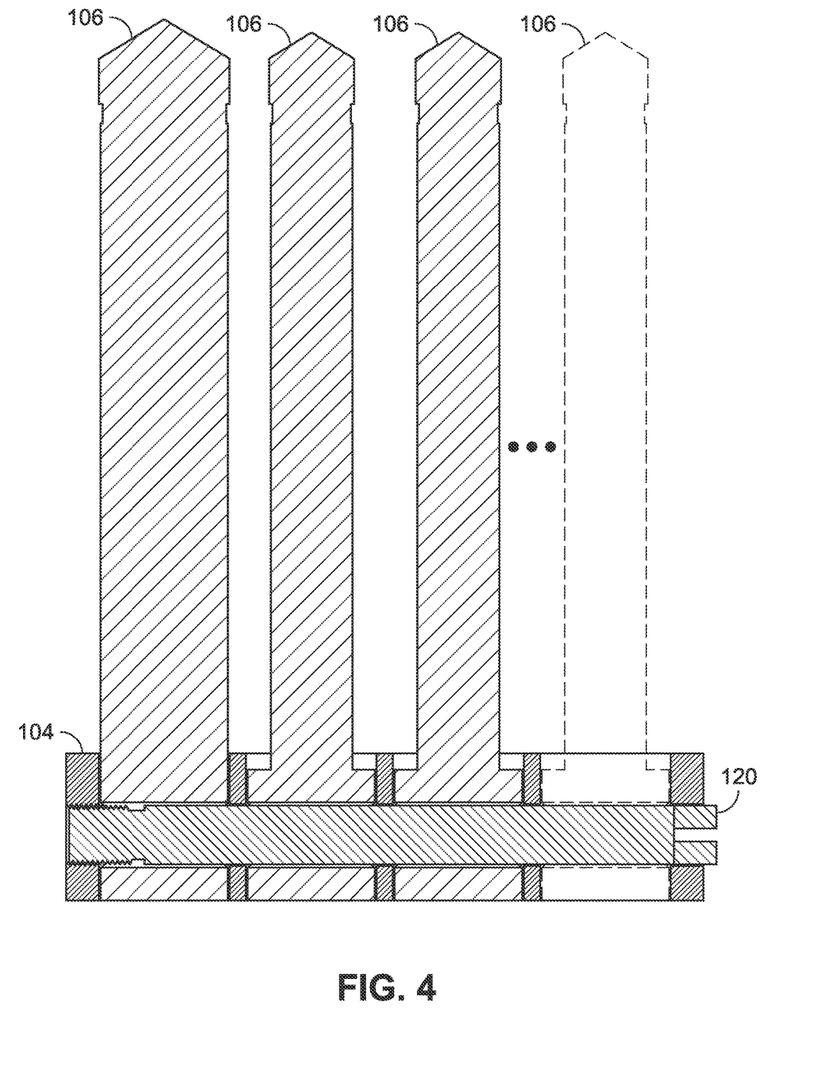
FIG. 4 is a cross-sectional view of a plurality of plungers coupled to a base of hydride generation assembly, illustrated in accordance with an embodiment of this disclosure.

In some embodiments, the two or more plungers 106 are movably coupled with the base 104. As shown in FIG. 4, for example, the plungers 106 are rotationally coupled to the base 104 with at least one pin 120 that extends through at least a portion of the base 104. Each plunger 106 is enabled to align itself with respect to its corresponding chamber (e.g., chamber 112, 114, or 116). In this regard, movement (e.g., tilting or wiggling) of the plungers 106 with respect to the base 104 can prevent or minimize jamming of the plungers 106 in their respective chambers 102. This can be used to account for manufacturing tolerance variations in the chambers 102 and/or the plungers 106. However, it should be noted that a pin connection between the plungers 106 and the base 104 is provided by way of example only and is not meant to limit the present disclosure. In other embodiments, the plungers 106 can be movably coupled with the base 104 using other connectors, such as ball-and-socket connectors, resilient connectors (e.g., rubber or spring-loaded connectors), or the like.

Figure 5:
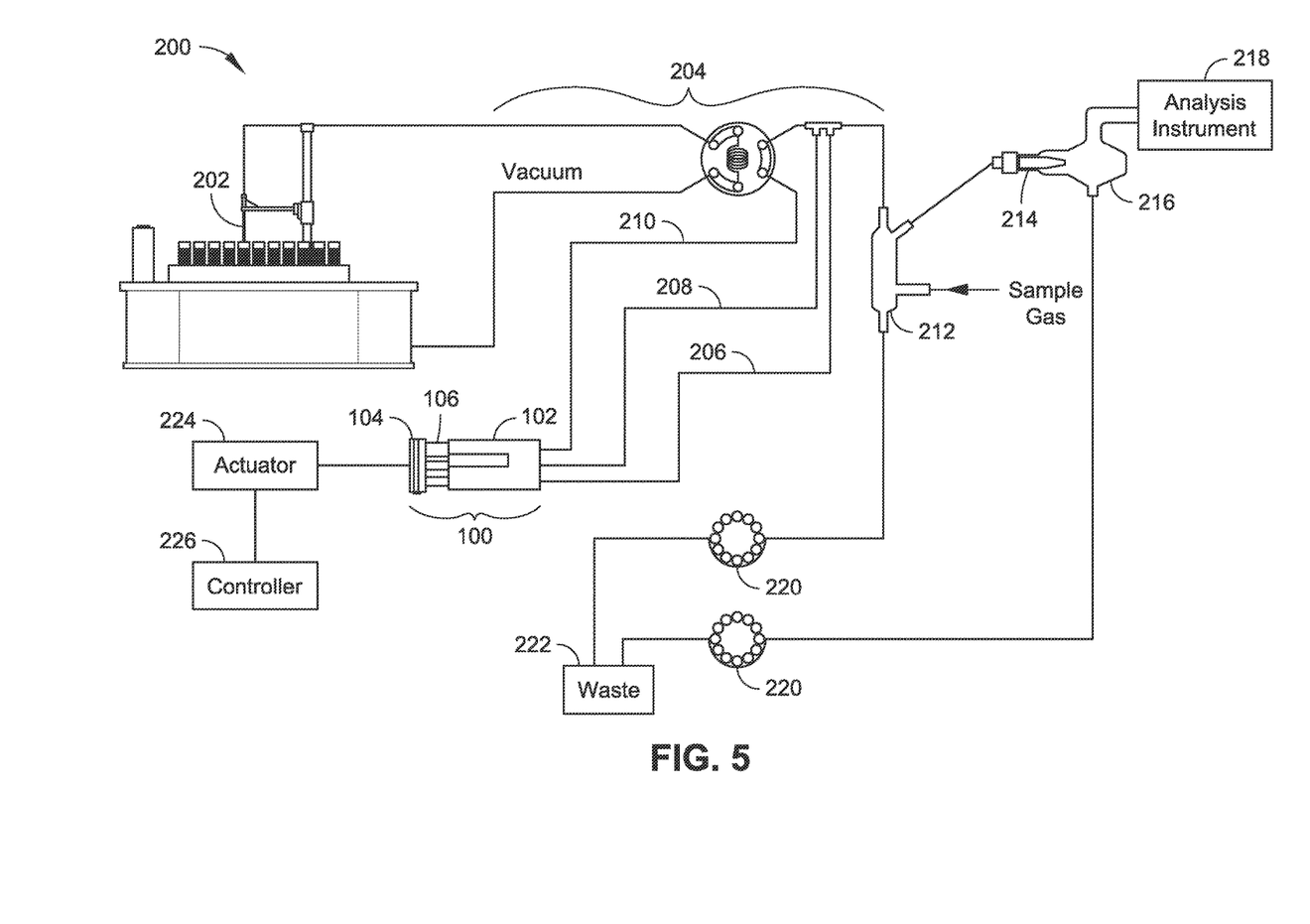
FIG. 5 is a schematic of an automated sampling system, illustrated in accordance with an embodiment of this disclosure.

An embodiment of a sampling system 200 is shown in FIG. 5. In some embodiments, the sampling system 200 includes a sampling assembly 202 (e.g., an automated syringe) configured to draw a selected amount of a sample into a mixing path 204 that may be defined by a network of tubes. In some embodiments, the sampling system 200 includes the hydride generation assembly 100 (also referred to as "system 100"), where the hydride generation assembly is configured to introduce selected amounts of a first hydride generation reagent and a second hydride generation reagent into the mixing path 204 via tubes (e.g., tubes 206 and 208) connected to respective ones of the chambers 102. For example, tube 206 may be connected to the first chamber 112 and tube 208 may be connected to the second chamber 114. In some embodiments, the hydride generation assembly is further configured to introduce a selected amount of a third fluid, such as a carrier solution or internal standard, into the mixing path 204 via a respective tube (e.g., tube 210) connected to a respective one of the chambers 102. For example, tube 210 may be connected the third chamber 116. Those skilled in the art will further appreciate that the hydride generation assembly 100 may further include a fourth chamber for introducing a fourth fluid into the mixing path or another fluid pathway, and so forth. A variety of changes can be made without departing from the scope of the present disclosure.

The sampling system 200 may further include a nebulizer 214 fluidically coupled with the mixing path 204. In some embodiments, a gas/liquid separator 212 is positioned between the mixing path 204 and the nebulizer 214. In the gas/liquid separator 212, gaseous substances formed by an interaction of the fluids in the mixing path 204 may be separated from liquid substances to remove liquids before entering the nebulizer 214. In some embodiments, the removed liquids may be pumped out of the separator 212 into a waste receptacle 222 via a peristaltic pump 220. The gaseous substances fed into the nebulizer 214 may include at least a portion of the sample. For example, gases in the mixing path 204 may include one or more gaseous mixtures or compounds generated by the sample and hydride generation reagents. After aerosolizing the received portions of the sample, the nebulizer 214 may be configured to introduce the portion of the sample received from the mixing path 204 into a spray chamber 216 that is either included within or coupled to an analysis instrument 218, such as an ICP spectrometry instrument (e.g., ICP-MS, ICP-OES, ICP-AES, or the like). The spray chamber 216 may be configured to direct at least a portion of the aerosol (e.g., fine aerosol particles) to an analysis site (e.g., torch or plasma site) of a sample analysis instrument 218.

In some implementations, the plungers 106 are enabled to move while the chambers 102 are held stationary to displace fluid within the chambers 102. For example, the base 104 may be driven an actuator 224 (e.g., an electrical motor, linear actuator, or the like) while the chambers 102 are mounted to a stationary structure. In other embodiments, the chambers 102 may be enabled to move while the plungers 106 are held stationary to displace fluid within the chambers 102. For example, the base 104 may be mounted to a stationary surface while a rigid structure (e.g., an armature or railing) coupled to the chambers 102 is moved by an actuator 224. In still further embodiments, both the plungers 106 and the chambers 102 are moved to displace fluid within the chambers 102. In some embodiments, the one or more actuators 224 are controlled by a controller 226, such as a general-purpose computer (e.g., workstation), a specific-purpose computer, an ASIC, a programmable logic device, a microcontroller, or the like. As used herein, the term "controller" can include electronic circuitry configured to perform a set of discrete operations and/or a processor configured to execute program instructions from a non-transitory storage medium (e.g., solid-state memory device, SD card, flash memory device, or the like). In some embodiments, the controller 226 is further configured to control valves, pumps, sampling assemblies, or other components of the sampling system 200.

Example Processes

Figure 6:
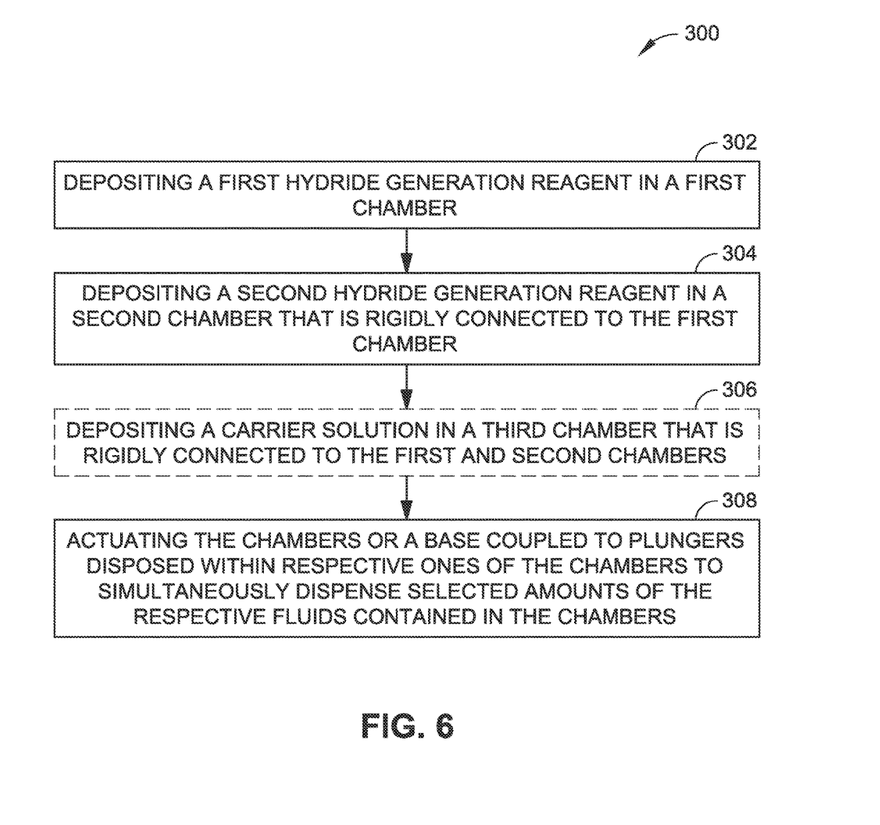

FIG. 6 is a flow diagram illustrating a method 300 of simultaneously introducing selected amounts of a first hydride generation reagent and a second hydride generation reagent into a mixing path or a mixing container. At step 302, a first hydride generation reagent (e.g., HCL) is deposited in a first chamber (e.g., chamber 112). At step 304, a second hydride generation reagent (e.g., $NaBH_4$, $SnCl_2$, or the like) is deposited in a second chamber (e.g., chamber 114) that is rigidly connected to the first chamber. Optionally, at step 306, a third fluid, such as a carrier solution or an internal standard, is deposited in a third chamber that is rigidly connected to the first and second chambers. At step 308, either the assembly of chambers (e.g., chambers 102) or a base that couples respective plungers (e.g., plungers 106) of the chambers is actuated to simultaneously dispense selected amounts of the respective fluids contained in the chambers. For example, the actuation of the assembly or the base may cause the first plunger to translate within the first chamber and the second plunger to translate within the second chamber to simultaneously output selected amounts of the first hydride generation reagent and the second hydride generation reagent. This can also cause a third plunger to translate within the third chamber to simultaneously output a selected amount of the carrier solution or any other fluid contained therein. As a result of the synchronized fluid output, the hydride generation reagents and any other fluids dispensed by the assembly of chambers are introduced into a mixing path or a mixing container in fixed ratios with one another.

Those skilled in the art will appreciate that several of the steps of method 300 may be performed in an alternative order than the order illustrated in FIG. 6 or described herein. Some of the steps may be performed simultaneously or at least partially overlapping in time. Furthermore, method 300 may include additional steps for carrying out any of the functions or operations described herein with regards to system 100 or system 200.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system, comprising:
    a first chamber configured to contain a first hydride generation reagent;
    a second chamber configured to contain a second hydride generation reagent;
    a first plunger configured to translate within the first chamber and cause a displacement of the first hydride generation reagent;
    a second plunger configured to translate within the second chamber and cause a displacement of the second hydride generation reagent; and
    a base coupling the first plunger and the second plunger together, the base vertically movable relative to the first chamber and the second chamber.

2. The system as recited in claim 1, wherein the first plunger and the second plunger are moveably coupled to the base.

3. The system of claim 2, wherein the first plunger and the second plunger are moveably coupled to the base by at least one pin extending through at least a portion of the base.

4. The system of claim 1, wherein the first chamber and the second chamber are rigidly connected with one another.

5. The system of claim 4, wherein the first chamber and the second chamber are portions of a common structure.

6. The system of claim 4, further comprising one or more mounting members rigidly connected to the first and second chambers, the one or more mounting members configured for affixing the first and second chambers to a rigid structure.

7. The system of claim 6, further comprising:
    an actuator coupled to the rigid structure or the base; and
    a controller configured to cause the actuator to actuate the rigid structure or the base to dispense a selected amount of the first hydride generation reagent and a selected amount of the second hydride generation reagent.

8. The system of claim 1, further comprising:
    a third chamber configured to contain a carrier solution; and
    a third plunger configured to translate within the third chamber and cause a displacement of the carrier solution, wherein the base further couples the third plunger with the first plunger and the second plunger together.

9. The system of claim 8, wherein a cross-sectional area of the first chamber is different from a cross-sectional area of the second chamber, or a cross-sectional area of the first chamber is different from a cross-sectional area of the third chamber, or a cross-sectional area of the second chamber is different from a cross-sectional area of the third chamber.

10. The system of claim 8, wherein the third plunger is coupled with the base, and the base and the third plunger together are movable relative to the third chamber.

11. The system of claim 1, wherein the first chamber and the second chamber are sized appropriately to dispense the first hydride generation reagent and the second hydride generation reagent in a ratio suitable for forming a hydride when mixed with a sample.

12. The system of claim 1, wherein the first plunger and the second plunger are configured respectively to displace fluid within the first chamber and the second chamber in a synchronized manner when the base, the first plunger, and the second plunger together are moved relative to the first chamber and the second chamber.

* * * * *